United States Patent [19]

Chen et al.

[11] Patent Number: 5,290,693

[45] Date of Patent: Mar. 1, 1994

[54] IMMOBILIZATION OF MICROORGANISMS OR ENZYMES IN POLYVINYL ALCOHOL BEADS

[75] Inventors: Kuo-Cheng Chen; Ying-Feng Lin, both of Hsinchu, Taiwan

[73] Assignee: National Science Council, Taipei, Taiwan

[21] Appl. No.: 910,788

[22] Filed: Jul. 8, 1992

[51] Int. Cl.$^5$ ............... C12N 11/04; C12N 11/08
[52] U.S. Cl. ................... 435/182; 435/180; 435/262.5
[58] Field of Search ............. 435/180, 182, 262.5

[56] References Cited

FOREIGN PATENT DOCUMENTS 64-5490  1/1989  Japan .
64-5491  1/1989  Japan .

OTHER PUBLICATIONS

S. Hashimoto and K. Furukawa, "Immobilization of activated sludge by PVA-boric acid method," *Biotechnology and Bioengineering*, 30, 52–59 (1987).

*Primary Examiner*—David M. Naff
*Attorney, Agent, or Firm*—Winstead Sechrest & Minick

[57] ABSTRACT

Microorganisms or enzymes are immobilized by using polyvinyl alcohol to form beads containing a microorganism or an enzyme. An aqueous solution of about 10 to about 20 wt % polyvinyl alcohol containing a microorganism or an enzyme is reacted with an aqueous solution of about 3 wt % to saturated boric acid for a period of about 10 minutes to about two hours to form gelled spherical beads. The beads are then hardened by treatment with an aqueous solution of about 3 to about 20 wt % phosphoric acid or phosphate for at least 30 minutes. Preferably, the polyvinyl alcohol has a degree of polymerization of about 1000 to about 3000 and a degree of saponification of about 70 to about 99 mol %. In an alternative embodiment, the boric acid solution can contain the phosphoric acid or phosphate. The microorganism can be an acclimatized activated sludge microorganism from agricultural or industrial waste water. The beads can be used for removing inorganic nitrogen and organic carbon in waste water treatment or in processes for making biochemical products.

16 Claims, No Drawings

IMMOBILIZATION OF MICROORGANISMS OR ENZYMES IN POLYVINYL ALCOHOL BEADS

BACKGROUND OF THE INVENTION

The present invention relates to a process for immobilizing microorganisms or enzymes, and more particularly to an immobilization process for preparing microbial or enzymatic beads by using polyvinyl alcohol (PVA).

In the years since 1980, the immobilization methods of microorganisms or enzymes, in which various natural or synthetic polymeric substances are used to bring about the immobilization of the activated microorganisms or enzymes, have received a great deal of attention and achieved some success in the industrial application, as exemplified by their applications in the production of biochemical products such as high fructose syrup, 6-APA, L-amino acid, etc. The representative polymeric substances that are commonly used in preparing the immobilized microbial or enzymatic beads include such substances as polyacrylamide, K-carrageenan, sodium alginate, agar, etc. Polyacrylamide is commonly used in view of the fact that it is a rather inexpensive material; nevertheless it is not suitable for use in immobilizing the living cells of microorganisms on the grounds that its monomer is toxic and that it is difficult to form beads of spherical shape, which is a desirable form characteristic for a continuous reactor. Therefore, polyacrylamide may be replaced by K-carrageenan, which is less toxic and is relatively easy to form spherical beads. However, K-carrageenan is an expensive commodity. Sodium alginate is an inexpensive material, which forms spherical beads easily. But it has a shortcoming that its gel strength is rather instable in a reaction solution containing phosphate, and sodium or potassium cations. The agar is a gelatinous material having a lack of sufficient mechanical strength to sustain a prolonged operation. The immobilization techniques of microorganisms afford a great deal of potential of improving the production process of biochemical products and the wastewater treatment. It is, therefore, important that we are in need of developing a new and inexpensive immobilization material which is not toxic to microorganisms and has an strong gel strength so as to ensure that the bead formation is successful.

Polyvinyl alcohol (PVA) is a water-soluble polymer; it has advantages that it is nontoxic to both human being and microorganisms, and that it is provided with a mechanical strength sufficiently strong enough to ensure the success of bead formation, and further that it is a polymeric substance which is commonly used in industry and produced in quantity economically. Therefore, PVA is an ideal substance for use in immobilizing microorganisms.

Various patented methods of immobilizing microorganisms by PVA have been disclosed in recent years, as exemplified by the Japanese patent applications Kokai 57-14129 (1982) and 61-139385 (1986) in which the entrapment methods are characterized in that the gelations of the mixture containing the PVA aqueous solution and the microorganisms are carried out by the methods associated with the freezing and thawing technique. Another Japanese patent application Kokai 1-454372 (1989) discloses a method, in which the mixture of the PVA aqueous solution and the microorganisms is exposed to the ultraviolet radiation so as to form a photocrosslinking gelation. Another gelation technique has to do with the formation of crosslinking structure by permitting the mixture of the PVA aqueous solution and the microorganisms to make contact with and the microorganisms to make contact with a saturated boric acid solution, as disclosed in an article by Susumu Hashimoto and Kenji Furukawa, entitled "Immobilization of Activated Sludge by PVA-Boric Acid Method", Biotechnology and Bioengineering, Vol. XXX, pp 52-59 (1987). In spite of the fact that the above-mentioned methods of the prior art can be used to prepare the immobilized beads having a relatively good gel strength, they have shortcomings that call for further improvement. The freezing and thawing method mentioned above is defective in that it is a tedious and costly process requiring the materials to be frozen, defrosted and dehydrated and that it must be carried out at the temperatures in a range of $-30°$ C. to $-80°$ C. The photocrosslinking method is not suitable for use in immobilizing microorganisms in view of the fact that it is generally used in making thin membranes. The PVA-boric acid method requires that the mixture of the PVA solution and the microorganisms remains in contact with the boric acid aqueous solution for a period of 12-24 hours so as to form beads having a relatively strong gel strength.

In short, the prior art described above share the following shortcomings. In the first place, they are time-consuming and complicated, thereby resulting in a substantial increase in the expenditure for largescale production facilities without increasing the productivity. Secondly, an environment in which cryogenic temperature, vacuum and boric acid are present is antagonistic to the living microorganisms intended to be immobilized. The Japanese patent application Kokai 64-5490 and 64-5491 (1989) disclose the methods in which the sulfate aqueous solution is used in place of the boric acid aqueous solution. Such methods are effective in shortening the time that is required for the immobilization process to be brought to a conclusion. However, such methods use the gel solutions having a relatively high concentration. Therefore, such methods must be carried out in the presence of an aqueous solution containing 30% of sodium sulfate or 70% of ammonium sulfate. If the concentration is too low, the bead formation and the gel strength will not be satisfactory. Therefore, such methods are costly. In addition, a high salt concentration used in the gelation process has an adverse effect on metabolism of microorganisms intended to be immobilized.

SUMMARY OF THE INVENTION

It is, therefore, the primary objective of the present invention to provide a simple, low-cost energy-saving and time-saving process for preparing polyvinyl alcohol-immobilized microbial or enzymatic beads for application in waste water treatment and biochemical industry.

It is another objective of the present invention to provide a two-step process for preparing polyvinyl alcohol-immobilized microbial or enzymatic beads, in which the mixture of PVA and microorganisms is treated for gelation in a 3 wt % to saturated boric acid solution and is subsequently hardened in an aqueous solution containing 3-20 wt % of phosphoric acid or phosphate. Such method can be carried out easily at a low cost, without subjecting the microorganisms to toxic substances. In addition, such method is superior to the prior art, in which the sulfate solution is used, in terms of the gel strength of beads so formed.

In keeping with the principles of the present invention, the foregoing objectives of the present invention are accomplished by an improved process for preparing polyvinyl alcohol-immobilized microbial or enzymatic beads. The improved process comprises treating an aqueous mixture of polyvinyl alcohol and microorganisms or enzyme with 3 wt % to saturated boric acid aqueous solution to form gelled spherical beads, wherein the improvement comprises said mixture of polyvinyl alcohol and microorganism or enzyme being treated with said boric acid aqueous solution for a period of 10 minutes to two hours, the resulting gelled spherical beads being removed from the mixture and being further hardened in 3-20 wt % phosphoric acid or phosphate aqueous solution for at least 30 minutes.

The principles and the features of the present invention are based on the fact that the bead formation is brought about by an ionic linking action between the hydroxyl of the PVA molecule and the boric acid molecule. However, the heads formed in the boric acid solution are devoid of sufficient gel strength and are therefore immersed in the phosphoric acid solution or the phosphate solution so as to enhance the gel strength of the microbial or enzymatic beads. The hardening of the beads is made possible by esterification taking place between PVA and phosphoric acid or phosphate. Therefore, such immobilized microbial or enzymatic beads have strong gel strength and water-resistant characteristic without being detrimental to the biochemical vitality of microorganisms or enzymes so immobilized.

Alternatively, both the gelling and the hardening of the beads are carried out simultaneously in an aqueous solution containing boric acid and phosphoric acid or phosphate for a period of time ranging between 30 minutes and 3 hours, preferably being 1-2 hours.

DETAILED DESCRIPTION OF THE INVENTION

The method of the present invention uses PVA having a degree of saponification being over 70% and a degree of polymerization being 1000-3000, preferably the degree of saponification being over 95% and the degree of polymerization being 1500-2000. The excessively low degree of polymerization results in a weak gel strength of the beads, while the excessively high degree of polymerization brings about a high viscosity, thereby making the process difficult to manage. Before mixing PVA with microorganisms or enzymes intended to be immobilized, PVA is diluted with water. The preferable concentration of PVA in the PVA aqueous solution is 10-20% by weight. The optimum time requirement for the entrapment of microorganisms or enzymes in a saturated boric acid is 15-30 minutes.

The microorganism or enzyme to be immobilized is used in the form of an aqueous solution. A highly concentrated microorganism or enzyme aqueous solution is preferable in comparison with a low concentrated solution. However, there is an upper limit on the microorganism or enzyme concentration in the aqueous solution due to the fluidity and the concentration thereof being in inverse proportion to each other. For example, a concentrated activated-sludge aqueous solution to be used in the present process preferably has a concentration less than 120 g/L (W/V), more preferably ranging from 30-90 g/L (W/V).

The polyvinyl alcohol aqueous solution and the microorganism or enzyme aqueous solution is mixed in weight ratio of 1:2 to 2:1.

The preferable concentration of phosphoric acid or phosphate aqueous solution ranges between 5% to 15% by weight, while the optimum time for keeping the beads in the phosphoric acid or phosphate solution ranges from one hour to two hours. The preparation of phosphate aqueous solution may be done by using sodium phosphate, sodium hydrogen phosphate, sodium dihydrogen phosphate, potassium phosphate, potassium hydrogen phosphate, potassium dihydrogen phosphate, ammonium phosphate, ammonium hydrogen phosphate, or ammonium dihydrogen phosphate.

The present invention discloses another embodiment, in which both the gelling and the hardening of the beads are carried out simultaneously in an aqueous solution containing 3 wt % to saturated boric acid and 3-20 wt % phosphoric acid or phosphate for a period of time ranging between 30 minutes and 3 hours, preferably being 1-2 hours.

The present invention is characterized in that the fundamental framework of gelation is permitted to establish in a boric acid solution for a limited period of time. As a result, the likelihood that the boric acid does some damage to the microorganisms or the enzymes is reduced to a minimum. The PVA-boric acid immobilization method disclosed in the article by Susumu Hashimoto and Kenji Furukawa, *Biotechnology and Bioengineering*, Vol. XXX, pp 52-59 (1987) suggests the contact time of boric acid ranging from 15 hours and 24 hours. It is beneficial to use the phosphate solution to carry out the hardening step by virtue of the facts that the phosphate solution acts as a buffer solution and that the element of phosphorus is an essential element required for energy metabolism of microorganisms. Therefore, the application of the phosphate solution in the hardening step of the microbial beads is not only harmless to the microorganisms but also favorable for vitalizing the microorganisms.

The PVA-immobilization process of the present invention can be used effectively to immobilize enzymes, industrial microorganisms, waste water treatment microorganisms, animal and plant cells, etc. Some of the enzymes that can be immobilized by the PVA-immobilization process of the present invention are fermentation yeasts, nitric bacteria, denitration bacteria, activated sludge microorganism, anaerobic sludge microorganisms, methanogens, denitrifying sludge microorganisms, etc.

EXAMPLE 1

An aqueous solution (20 g.) containing 15% by weight of PVA (99% saponification, 2000 degree of polymerization) was mixed thoroughly with a concentrated solution (20 g.) of denitrifying sludge microorganisms (sludge concentration 50 g/L). This mixture was then added into a gently stirred saturated boric acid aqueous solution drop by drop to form spherical beads having a diameter on the order of 3 mm. Such spherical beads were allowed to remain in the saturated boric acid for 20 minutes. Thereafter, these beads were taken out by filtration and transferred to an aqueous solution containing 8% by weight of sodium dihydrogen phosphate and remained therein for 40 minutes. These beads are then taken out and rinsed with water. The 20 g of these immobilized microbial beads were mixed with 80 ml of waste water containing 100 ppm potassium nitrate and 350 ppm methanol. This mixture was kept in a serum bottle to undergo the denitrification. After being cultivated for two hours, the concentration of nitrate in the mixture was reduced to 32 ppm.

By using the same immobilized microbial beads and the new synthetic waste water, the same denitrification experiment was repeated. On the seventh day, denitrification rate of the immobilized microorganisms reached 0.65 mg $NO_3^1$-N/g gel/h, which remained unchanged until the 30th day. The biochemical vitality of microorganisms remained stable. The method disclosed in the article by Susumu Hashimoto and Kenji Furukawa was used as a control, wherein the same experimental procedures as above were repeated except that the phosphate aqueous solution was not used and the contact time with the boric acid solution was 24 hours. After being cultivated for 24 hours, the concentration of nitrate in the waste water was 82 ppm. The denitrification rate was 0.55 mg $NO_3^1$-N/g gel/h on the 15th day of the experiment. Thereafter, the rate remained quite unstable.

EXAMPLE 2

An aqueous solution containing 20% of PVA by weight (99% saponification, 2000 degree of polymerization) was mixed in 1:1 weight ratio with a concentrated solution (sludge concentration of 30 g/L) of nitrifying sludge. This mixture was then treated in the same manner as described in Example 1.

The immobilized microbial beads so produced have a diameter of about 3 mm. Such beads were kept in a 10 L bioreactor, into which an aqueous stream containing 200 ppm of ammonia nitrogen was introduced at the flowing rate of 30 L/day. The loading rate of the beads was 25%, while the aeration rate was 20 L/min. After such continuous operations for ten days, the concentration of ammonia nitrogen in the effluent was found to be 9 ppm, with 92% of ammonia nitrogen having been converted into the nitric acid nitrogen.

EXAMPLE 3

The activated sludge, which was tamed (or acclimatized) for a period of one month by means of the pig industry waste water (1500-2000 ppm COD concentration, 200-300 ppm total nitrogen concentration), was used to make a concentrated sludge solution by centrifugation. This concentrated sludge solution was mixed in 1:1 weight ratio with an aqueous solution containing 18% by weight of PVA (99% saponification, 2000 degree of polymerization). This mixture was added into an aqueous solution containing 5% by weight of boric acid and 10% by weight of potassium dihydrogen phosphate drop by drop to form spherical beads. Such beads, which had a diameter of about 3 mm, were kept in the solution for one hour. The immobilized microbial beads were then kept in a bioreactor, as described in Example 2, for carrying out the treatment of waste water from the pig industry. The operational conditions of the bioreactor were the same as those described in Example 2. After a 20-day continuous operation, the COD concentration of effluent was reduced to 200-300 ppm, while the total nitrogen concentration was reduced to 120-180 ppm.

EXAMPLE 4

A 10 g of centrifugally concentrated aqueous solution containing cells (30 g/L concentration) of fermentation yeast, *Sacchramyces cerevisa*, was mixed with a 10 g of aqueous solution containing 20% by weight of PVA (99% saponification, 2000 degree of polymerization). This mixture was treated in the same manners as described in Example 1. The immobilized cell beads were found to have a diameter of about 2 mm. The beads in the amount of 15 g were mixed with 150 ml of the culture medium containing 3% by weight of glucose. This mixture was kept in a flask, which was then cultivated on a shaker at the temperature of 30° C. for 8 hours. The concentration of alcohol produced in the culture was found to be 10.2 g/L. With the same amount of isolated fermentation yeast and under the same cultivating conditions, the concentration of alcohol in the culture was 10.6 g/L.

EXAMPLE 5

A 10 g of concentrated aqueous solution containing cells (20 g/L concentration) of a steroid converting bacterium, *Arthrobacter simplex* was mixed with a 10 g of aqueous solution containing 20% by weight of PVA (99% saponification, 2000 degree of polymerization). This mixture was treated in the same manners as described in the Example 3. The immobilized cell beads were found to have a diameter of about 2 mm. The beads in the amount of 15 g were mixed with the 150 ml of a culture medium containing 0.2 g/L of hydrocortisone. This mixture was then kept in a flask having a capacity of 500 ml. The culture contained in the flask was caltivated on a shaker for five hours. The result of such $\Delta^1$-dehydrogen biochemical reaction of steroid showed that 90% of the hydrocortisone had been converted into the prednisolone.

EXAMPLE 6

An aqueous solution in amount of 10 g containing 15% by weight of PVA (99% saponification, 2000 degree of polymerization) was mixed with a solution in amount of 3 g containing isoamylase and a solution in amount of 2 g containing $\beta$-amylase. This mixture was treated for immobilization of enzymes in the same manners as described in the Example 1. The immobilized enzymatic beads so formed were found to have a diameter of about 2 mm. These enzymatic beads in amount of 15 g were mixed with the 150 ml of a medium solution containing 50 g/l of liquedified starch. Such mixture was kept in a flask having a capacity of 500 ml. The culture contained in the flask was cultivated on a shaker for 3 hours. The result of the starch hydrolysis showed that the concentration of sucrose reached as high as 40 g/L, and that the starch conversion rate was 82%.

What is claimed is:

1. A process for preparing polyvinyl alcohol-immobilized microbial or enzymatic beads, said process comprising the steps of:

reacting about a 10 to about a 20 wt % aqueous solution of polyvinyl alcohol and a microorganism or an enzyme with about 3 wt % to saturated boric acid aqueous solution for a period of about 10 minutes to about two hours to form gelled spherical beads, wherein said polyvinyl alcohol has a degree of polymerization from about 1000 to about 3000 and a degree of saponification from about 70 to about 99 mol %;

removing said gelled spherical beads from said reaction mixture; and hardening said gelled spherical beads by treating said gelled spherical beads with about a 3 to about a 20 wt % phosphoric acid or phosphate aqueous solution for at least 30 minutes.

2. A process for preparing polyvinyl alcohol-immobilized microbial or enzymatic beads, said process comprising the steps of:

reacting about a 10 to about a 20 wt % aqueous solution of polyvinyl alcohol and a microorganism or an enzyme with about 3 wt % to saturated boric acid aqueous solution for a period of about 30 minutes to about three hours to form gelled spherical beads, wherein said boric acid aqueous solution further comprises about 3 to about 20 wt % phosphoric acid or phosphate and said polyvinyl alcohol has a degree of polymerization from about 1000 to about 3000 and a degree of saponification from about 70 to about 99 mol %; and recovering said spherical beads from said aqueous solution.

3. The process of claim 1 wherein said boric acid aqueous solution is a saturated boric acid aqueous solution, and said mixture of polyvinyl alcohol and microorganism or enzyme is treated with said boric acid aqueous solution for a period of 15-30 minutes.

4. The process of claim 1 wherein said phosphoric acid or said phosphate aqueous solution has a concentration of 5-15% by weight and said gelled spherical beads are hardened in said phosphoric acid or phosphate aqueous solution for 1-2 hours.

5. The process of claim 2 wherein said boric acid aqueous solution contains saturated boric acid and 5-15 wt % of phosphoric acid or phosphate.

6. The process of claim 2 wherein said period is 1-2 hours.

7. The process of claim 1 wherein said phosphate is selected from the group consisting of sodium phosphate, potassium phosphate, ammonium phosphate, and acid salts thereof.

8. The process of claim 2 wherein said phosphate is selected from the group consisting of sodium phosphate, potassium phosphate, ammonium phosphate, and acid salts thereof.

9. The process of claim 1 wherein said polyvinyl alcohol has a degree of polymerization from about 1500 to about 2000 and a 95-99 mol % degree of saponification.

10. The process of claim 2 wherein said polyvinyl alcohol has a 1500-2000 degree of polymerization and a 95-99 mol % degree of saponification.

11. The process of claim 1 wherein said microorganism is bacteria, fungi, algae, or protozoda.

12. The process of claim 2 wherein said microorganism is bacteria, fungi, algae, or protozoda.

13. The process of claim 1 wherein said microorganism is an acclimatized activated sludge microorganism of agricultural or industrial waste water.

14. The process of claim 2 wherein said microorganism is an acclimatized activated sludge microorganism of agricultural or industrial waste water.

15. The process of claim 1 wherein said enzyme is amylase, cellulase, or proteinase.

16. The process of claim 2 wherein said enzyme is amylase, cellulase, or proteinase.

* * * * *